US00PP25068P2

(12) United States Plant Patent
Kim et al.

(10) Patent No.: US PP25,068 P2
(45) Date of Patent: Nov. 18, 2014

(54) APPLE TREE NAMED 'HWANGOK'

(50) Latin Name: ***Malus domestica* Borkh.**
Varietal Denomination: Hwangok

(75) Inventors: Mok-Jong Kim, Gyeongbuk (KR); Soon-Il Kwon, Gyeongbuk (KP); Jong-Chul Nam, Gyeongbuk (KR); Pong-Nyol Paek, Gyeongbuk (KR)

(73) Assignee: The Rural Development Administration, Republic of Korea (KR)

( * ) Notice: Subject to any disclaimer, the term of this patent is extended or adjusted under 35 U.S.C. 154(b) by 91 days.

(21) Appl. No.: 13/374,392

(22) Filed: Dec. 27, 2011

(51) Int. Cl.
*A01H 5/00* (2006.01)

(52) U.S. Cl.
USPC ..... Plt./172

(58) Field of Classification Search
CPC ..... A01H 5/0875; A01H 5/00
USPC ..... Plt./172, 168
See application file for complete search history.

(56) References Cited

U.S. PATENT DOCUMENTS

| | | | | |
|---|---|---|---|---|
| PP7,001 | P | 8/1989 | Hiraragi | |
| 6,723,680 | B2 | 4/2004 | Chung et al. | |
| PP18,541 | P2 * | 3/2008 | Tupy et al. | Plt./172 |
| PP20,190 | P2 * | 7/2009 | Orozco | Plt./172 |
| 2005/0032646 | A1 | 2/2005 | Nahm et al. | |

FOREIGN PATENT DOCUMENTS

| | | |
|---|---|---|
| KR | 4207 | 11/2012 |
| WO | 0165921 A1 | 9/2001 |

OTHER PUBLICATIONS

PLUTO: Plant Variety Database, citation for Apple plant named 'Hwangok' (KR PBR 1020100000143, filed Feb. 5, 2010) (https://www3.wipo.int/pluto/user/en/index.jsp, Jun. 17, 2013).*
"Dave's Garden, Plant Files: Detailed Information on Apple Malus×Domestica 'Kogetsu'", Retrieved from web on Nov. 20, 2012, <http://davesgarden.com/guides/pf/go/160630/, pp. 1-2.

* cited by examiner

*Primary Examiner* — June Hwu
(74) *Attorney, Agent, or Firm* — MacMillan, Sobanski & Todd, LLC

(57) ABSTRACT

A new and distinct variety of apple tree variety 'Hwangok' is described herein. The 'Hwangok' apple tree produces fruit that is round, medium-sized, and has a surface that is yellow-green with variable red patches.

9 Drawing Sheets

STATEMENT REGARDING U.S. FEDERAL FUNDING

Research related to this invention was not made with any United States Government support and the United States Government has no rights in the invention.

Genus and species: *Malus domestica* Borkh.
Variety denomination: 'Hwangok'.

BACKGROUND OF THE INVENTION

I. Field & Utility Summary

The present invention relates to a new and distinct variety of apple tree. The apple tree is particularly useful in that it can be propagated clonally and provides distinctive fruit attributes.

II. Cultivation Summary

'Hwangok' originated from a planned cross in 1994 in Korea. The seed parent was 'Kogetsu' and the pollen parent was 'Yataka'.

III. Parental Comparisons

'Hwangok' is similar to parent 'Kogetsu' (unpatented) in fruit size. 'Hwangok' differs from parent 'Kogetsu' in fruit shape and color. 'Hwangok' fruit is round, with a surface that is yellow-green with variable red patches, whereas parent 'Kogetsu' fruit is conical and its surface is red.

'Hwangok' is similar to parent 'Yataka' in fruit maturation timing. 'Hwangok' differs from parent 'Yataka' (U.S. Plant Pat. No. 7,001 P) in fruit shape, size, and color. 'Hwangok' fruit is globose, medium-sized, with a surface that is yellow-green with variable red patches covering about 10% surface area and patch color RHS 40D when ripe, whereas parent 'Yataka' fruit is oblate, large, and its surface is red.

'Hwangok' is different from both parents 'Kogetsu' and 'Yataka' because 'Hwangok' fruit is globose, medium-sized, and has a surface that is yellow-green with variable red patches.

IV. Closest Non-Parental Comparator

'Hwangok' differs from non-parent comparator 'Hongro' in fruit size, color, and flower petal position. 'Hwangok' fruit is small to medium-sized, has a surface that is yellow-green with variable red patches, and flowers that have distant relative position of petals, whereas 'Hongro' fruit is small, has a red surface, and flowers that have adjacent relative position of petals.

V. Breeding History

In 1994, pollen from a 'Yataka' apple tree was applied to emasculated flowers of a 'Kogetsu' apple tree in Korea. Between 1995 and 2004, the seeds derived from this pollination were extracted from mature fruit derived from this cross and screened to obtain favorable seedlings. Between 2005 and 2009, the seeds were screened and regional adaptability tests were carried out before a single plant from the stated cross was selected and named 'Hwangok' in 2009. The 'Hwangok' plant was then expanded by asexual propagation for five generations.

VI. Asexual Reproduction

Asexual reproduction of 'Hwangok' has been achieved using traditional grafting techniques. Five centimeter sections of branches from a 'Hwangok' plant were cut, and grafted onto pieces of M.9 rootstock stem, in Gunwi-gun/Gyeongsangbuk-do, in the Republic of Korea. Approximately three buds were present on each 5 cm branch piece. The grafted plant was grown under standard conditions, in Gunwi-gun/Gyeongsangbuk-do, in the Republic of Korea.

VII. Stability

Observations of trees from clonal propagations indicate that all trees have proven true to type and identical in all appearances to the original tree. No genetic variations were found, and therefore, its traits are stable.

SUMMARY OF THE INVENTION

'Hwangok' apple tree produces fruit that is globose, medium-sized, and has a surface that is yellow-green with variable red patches of about 10% surface area and patch color RHS 40D when ripe.

DETAILED BOTANICAL DESCRIPTION

Figure 1:
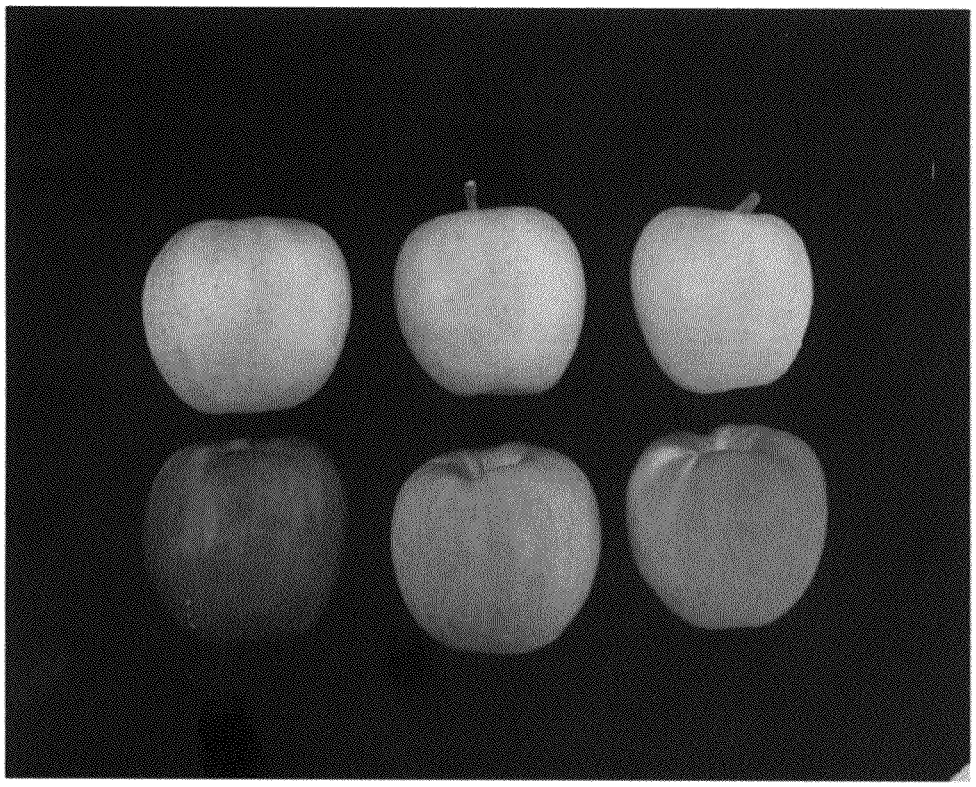
FIG. 1 shows the fruits of 'Hwangok' (up) and a similar non-parental comparator variety 'Hongro' (down).
Figure 2:
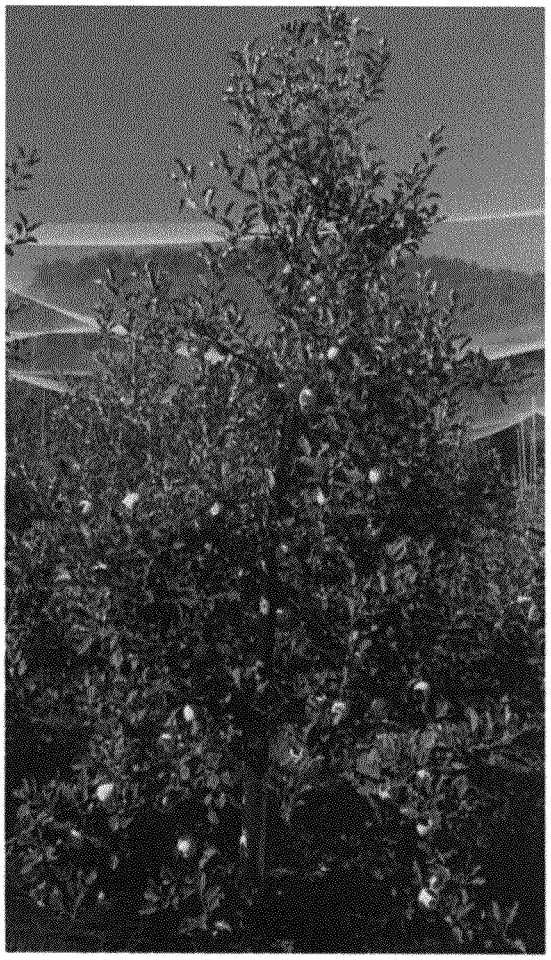
FIG. 2 shows the live plant 'Hwangok'
Figure 3:
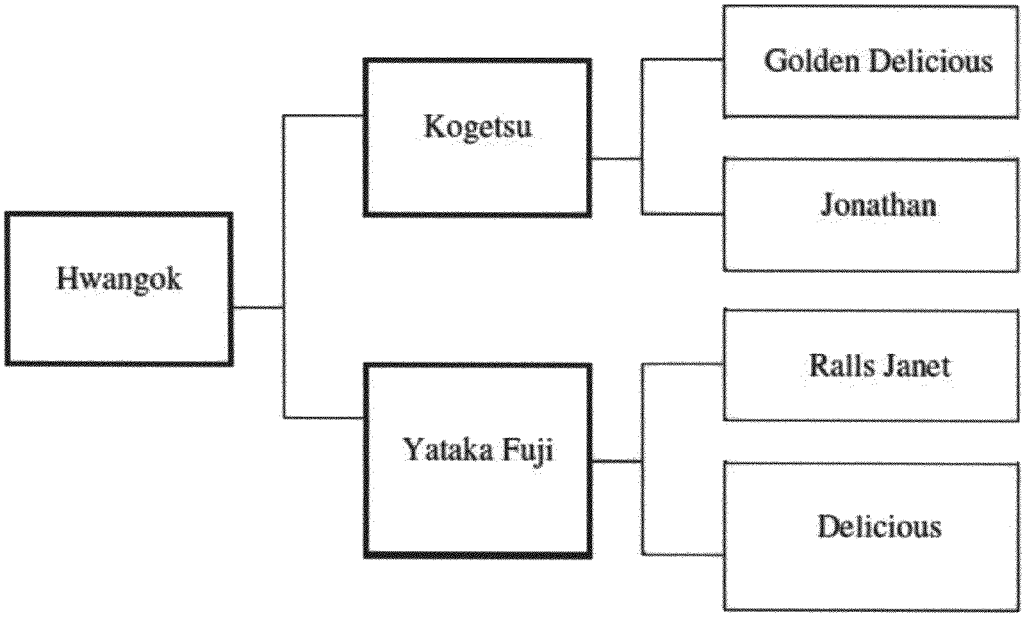
FIG. 3 is a schematic of the parentage of 'Hwangok'.
Figure 4:
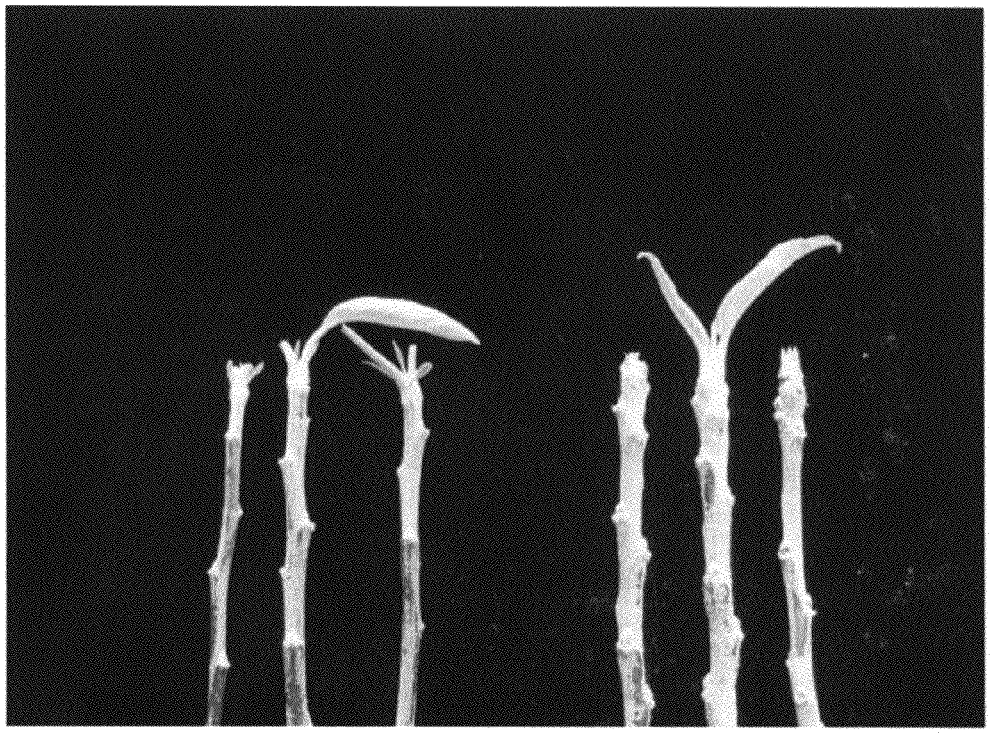
FIG. 4 shows actively growing shoot of 'Hwangok'.
Figure 5:
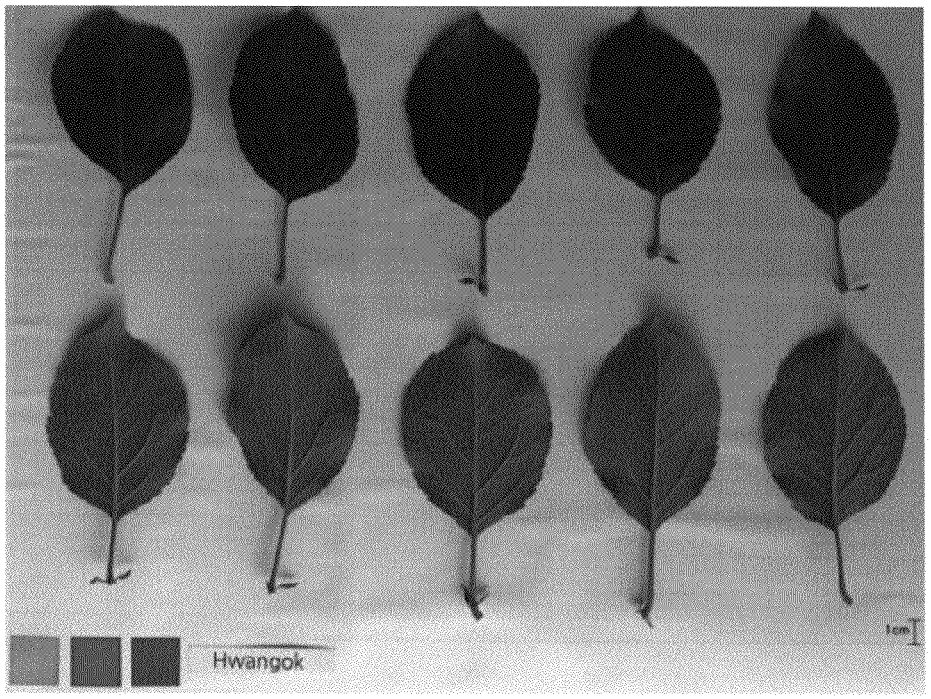
FIG. 5 shows the adaxial (upper) and abaxial (lower) surface of mature leaves of 'Hwangok'.
Figure 6:
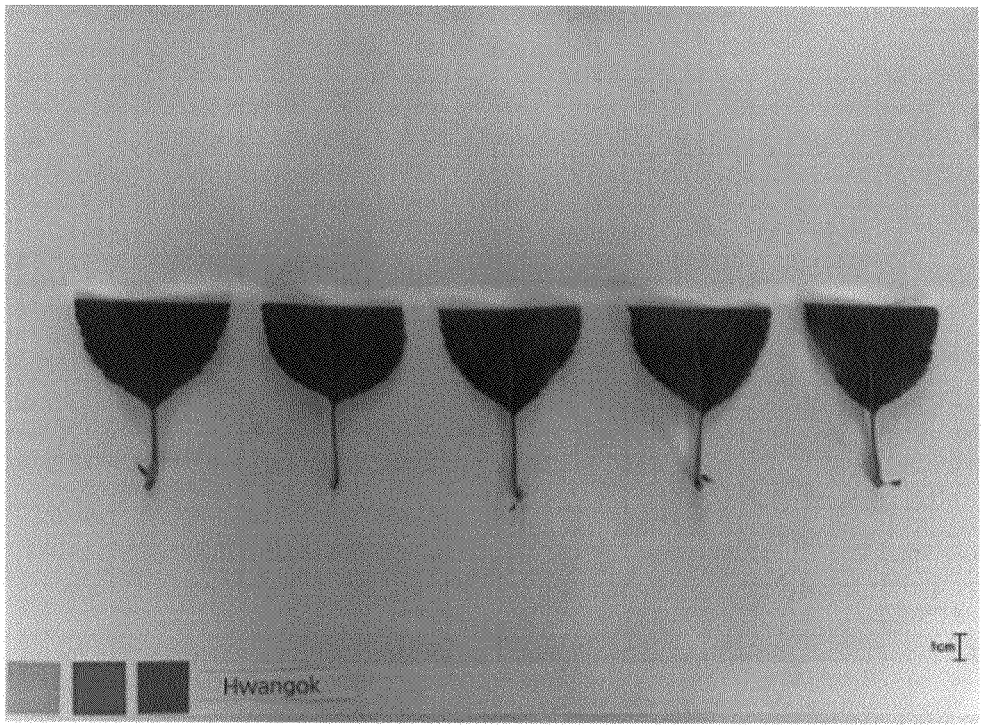
FIG. 6 shows the adaxial (upper) cut surface of leaves of 'Hwangok'.
Figure 7:
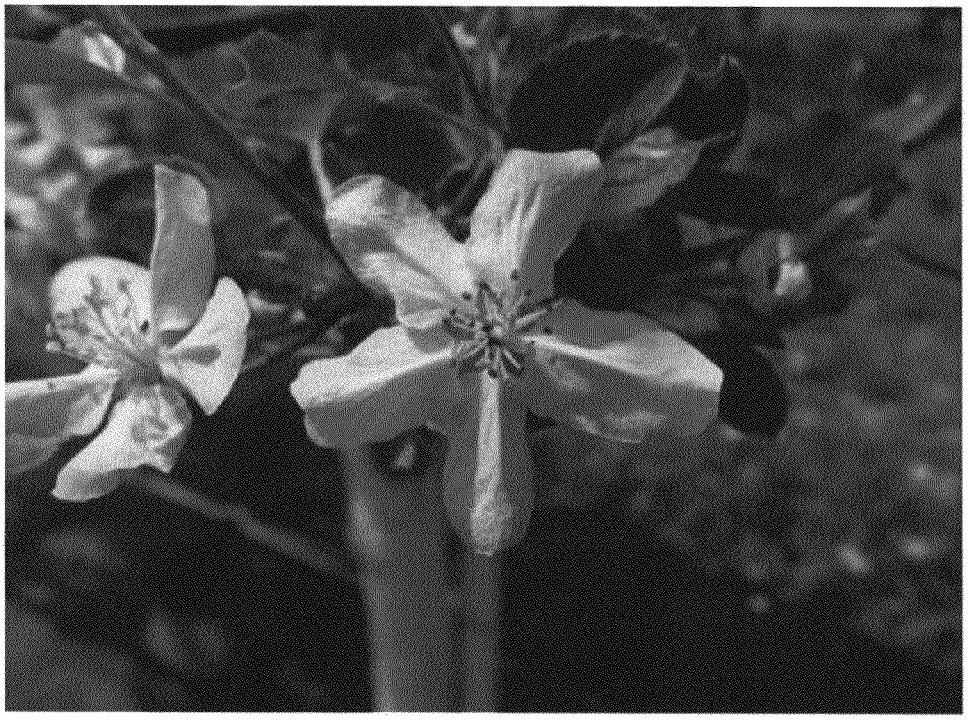
FIG. 7 shows typical inflorescence of 'Hwangok'.
Figure 8:
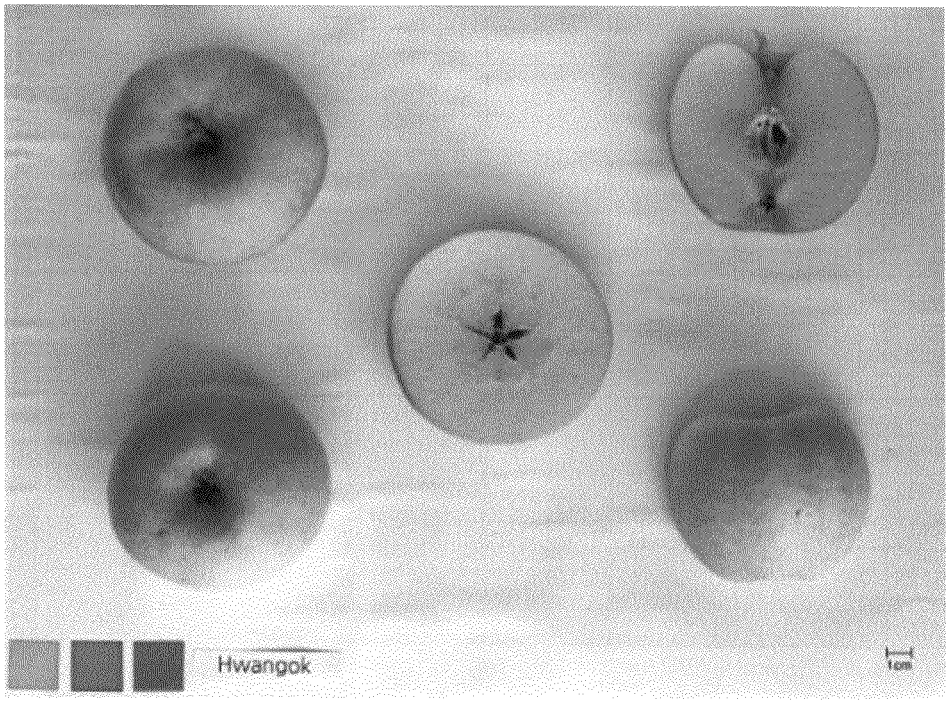
FIG. 8 shows various aspects of the fruit of 'Hwangok', including a view of the cavity (stem end), basin (calyx end), side view, a transverse sectional and a longitudinal sectional, showing the seeds, flesh and outer skin.
Figure 9:
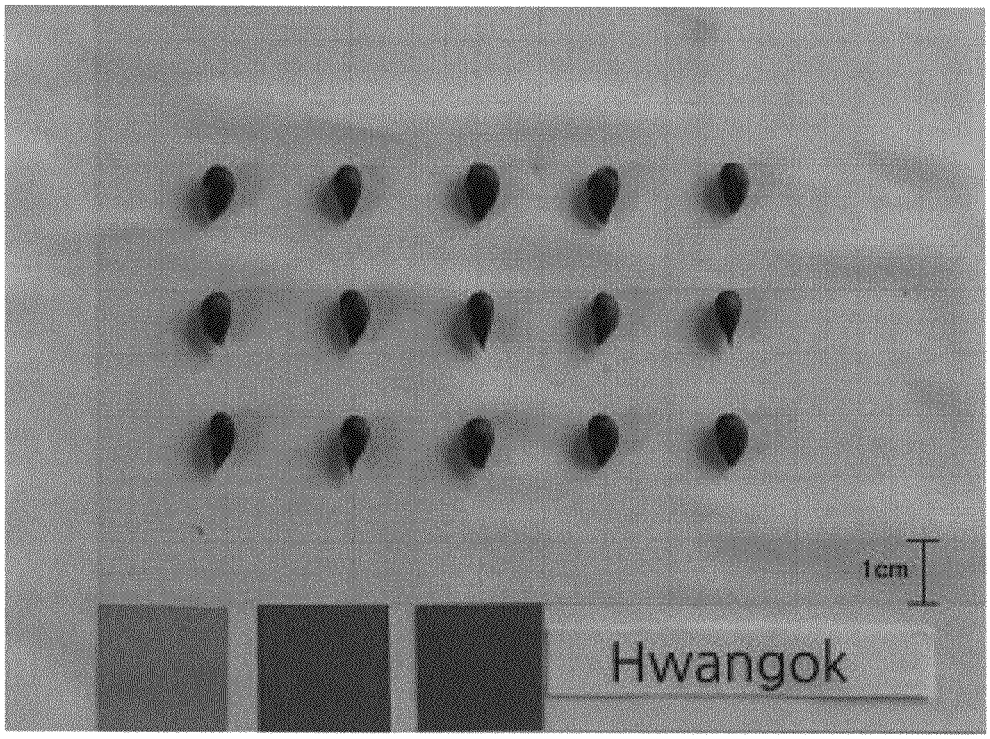
FIG. 9 shows seeds of 'Hwangok'.

The following description of 'Hwangok' contains references to color names taken from The Royal Horticultural Society Colour Chart (R.H.S.), 2001 edition. Botanical descriptions follow the Manual of Cultivated Plants (Bailey, 1949). The botanical information below is from when the 'Hwangok' plant was grafted, at 6 years old.

Tree:

*Habit*.—Upright-semi-spreading.

*Size*.—Height: 4.5 m. Width: 2 m.

Stem: 1 year old branches at top of the trunk:

*Color* (*RHS*).—199A.

*Length*.—45 cm.

*Diameter*.—6.3 mm.

*Pubescence*.—Strong.

*Shape*.—Straight.

*Odor* (*of bruised stem*).—None.

*Internode length*.—2.48 cm.

Leaves:

*Leaves*.—Leaf arrangement: Alternate. Shape: Ovate.

*Mature size*.—Length: 5.42 cm. Width: 4.40 cm.

*Apex*.—Sharp.

*Base*.—Narrow.

*Margin*.—Serrate type 1.

*Upper surface*.—Color (RHS): 141A. Texture: Rough.

*Lower surface*.—Color (RHS): 134A. Texture: Rough.

*Venation*.—There are five on each side, and arranged asymmetric.

*Pubescence*.—Medium.

*Lobes* (*present/absent*).—Absent.

*Petiole*.—Length: 31.55 mm. Shape: Straight. Color (RHS): 140B. Pubescence: Medium. Diameter: 1.8 mm.

Flowers:

*Inflorescence*.—Number of individual flowers per stem: 5.

*Individual flower*.—Symmetry: Asymmetrical. Bloom diameter 40 mm. Petals: Shape: cylindrical. Apex: RHS 155D. Base: RHS 155D. Margin: RHS 155D. Color at peak of bloom: Upper: RHS 155D. Center: RHS 62A.

*Pedicels*.—Color (RHS):177D. Pubescence: Medium. Length: 29.9 mm.

*Sepals*.—Number: 5. Size (L×W): 7 mm×7 mm. Shape: Triangle. Pubescence: Medium. Color (RHS): 155D.

*Stamens*.—Number: 18. Size (L×W): L 20 mm. Color (RHS): 4A. Pollen color (RHS): 4A. Pubescence: Weak.

*Pistils*.—Number: 5. Size of style (L×W): L 21 mm. Color of style (RHS): 4D. Color of stigma (RHS): 4D.

*Bracts*.—Number: 12. Size (L×W): L 16 mm×W 10 mm. Color (RHS): 134B. Shape:

Bud/spur, bloom time, harvest season:

| Variety | YEAR | Bud time (Month.Day) | Bloom time (Month.Day) | Harvest maturity (Month.Day) |
|---|---|---|---|---|
| Hwangok | 2007 | 3.26 | 4.23 | 9.27 |
| | 2008 | 3.24 | 4.20 | 9.18 |
| | 2009 | 3.20 | 4.16 | 9.18 |
| | On average | 3.23 | 4.20 | 9.21 |

Pollinator requirements: Self-incompatibility of 'Hwangok' is 'S3S9', and 'Hwangok' has affinity with 'Fuji', 'Gala' and 'Golden Delicious', so it does not require artificial pollination.

Fruit:

*Size*.—Height: 69.8 mm. Diameter: 76.8 mm. Weight: 233 g.

*Shape*.—Globose. Color (RHS): 160B.

*Flesh*.—High firmness (3.5 kgf 8 mm).

*Sepal*.—7 *mm*×7 mm.

*Calyx*.—Size: 7 mm×7 mm.

*Flesh*.—Color (RHS): 150D. Taste: Good.

*Skin color*.—Yellow Green (RHS 154A).

*Skin sheen*.—Normal.

*Aperture eye stalk bloom*.—Deep (30.1 mm).

*Percent soluble solids*.—15.0°.

*Titratable acidity*.—0.48%.

*Penetrometer*.—34.32N.

Seed:

*Color* (*RHS*).—200D.

*Size*.—Height: 8.5 mm. Diameter: 3.5 mm.

*Number*.—8.

*Keeping/storing*.—20 days at room temperature.

*Core size*.—Medium.

*Aroma*.—Light fragrance.

Disease resistance: Resistance to bitter rot, Anthrax and Leaf spot.

The invention claimed is:

1. A new and distinct variety of apple tree named 'Hwangok' as described and illustrated herein.

* * * * *